United States Patent [19]
Ebing et al.

[11] 3,933,437
[45] Jan. 20, 1976

[54] APPARATUS FOR AUTOMATICALLY PURIFYING EXTRACTS OF VEGETABLE AND ANIMAL SPECIMENS FOR THE DETERMINATION FREE FROM INTERFERENCE OF TRACES OF SELECTED EXTRACT CONSTITUENTS

[76] Inventors: Winfried Ebing, Trautenaustrasse, 1 Berlin 31; Jochen Pflugmacher, 67, Hochsitzweg, 1 Berlin 37, both of Germany

[22] Filed: Sept. 5, 1973

[21] Appl. No.: 394,586

[30] Foreign Application Priority Data
Sept. 6, 1972 Germany............................ 2243650

[52] U.S. Cl................ 23/253 R; 23/259; 23/267 R; 23/267 MS; 426/231; 426/331
[51] Int. Cl.² .................. B01D 11/00; G01N 33/02; G01N 33/16
[58] Field of Search.. 23/259, 253 R, 232 C, 230 R, 23/267 C, 267 MS, 267 R; 426/231, 331, 335

[56] References Cited
UNITED STATES PATENTS

| | | | |
|---|---|---|---|
| 3,199,956 | 8/1965 | Ferrari | 23/267 C |
| 3,424,557 | 1/1969 | Skeggs | 23/253 R |
| 3,589,868 | 6/1971 | Hozumi | 23/253 R X |
| 3,607,073 | 9/1971 | Stamm | 23/232 C X |
| 3,669,629 | 6/1972 | Paramonov | 23/259 |
| 3,765,461 | 10/1973 | Keck | 23/259 X |
| 3,794,467 | 2/1974 | Adams et al. | 23/253 R X |
| 3,811,842 | 5/1974 | Diebler et al. | 23/259 |

*Primary Examiner*—Joseph Scovronek
*Attorney, Agent, or Firm*—John C. Smith, Jr.

[57] ABSTRACT

An automatically controlled apparatus for purifying extracts of vegetable and animal specimens for the determination free from interference of traces of selected extract constituents by a combined flushing and codistilling process of the extracts with solvents comprises for the reception of samples detachable sample coils through which an inert gas stream obtained from a source of supply and carrying a solvent flowing substantially continuously from a supply vessel is conducted and purifying tubes which are connected to said sample coils and extend through a stove and terminate in cooling coils in receivers.

7 Claims, 2 Drawing Figures

APPARATUS FOR AUTOMATICALLY PURIFYING EXTRACTS OF VEGETABLE AND ANIMAL SPECIMENS FOR THE DETERMINATION FREE FROM INTERFERENCE OF TRACES OF SELECTED EXTRACT CONSTITUENTS

BACKGROUND OF THE INVENTION

This invention relates to apparatus for automatically purifying extracts of vegetable and animal specimens for the determination free from interference of traces of selected extract constituents.

SUMMARY OF THE INVENTION

The general aim of the invention is to provide apparatus which will permit a number of raw extracts of biological material to be automatically consecutively sufficiently purified without supervision to permit traces of particular organic-chemical substances contained in the extracts, such as impurities or active substances, to be determined.

The quantitative determination of traces of organic-chemical active substances, such as of residues of insecticides in foodstuffs, usually involves the following procedural steps:

1. Concentration of the substances that are to be measured by the preparation of an extract of the substrates in question.
2. Purification of the extract in such a manner that all substances, such as waxes, fats and dyes, which would interfere with the determination of the active substances (e.g. by gas chromatography and UV spectrophotometry) are removed.
3. Identification and quantitative analysis of the active substances.

The more specific object of the invention is to provide apparatus for carrying out the second above procedural step on a large number of samples of different kinds and composition containing required evaporable organic-chemical substances in extract form, by time-saving standardized procedures with the substantial elimination of manual control and supervision.

For the preparation of extracts for the trace analysis of organic-chemical substances several methods are available which are adapted to the individual peculiarities of the different samples and to the properties of the trace substances that are to be identified. Closest to the present invention is an instrument which operates on the basis of a flushing and codistillation process, and which substantially consists of glass tubes filled with glass wool having a Tee fitting at one end and a ground spigot at the other end for connection to a flexible cooling tube. The side branch of the Tee fitting is connected to the carrier gas supply, whereas the other branch is closed by a rubber disc (septum). The arrangement works by first taking up a sample with an injection syringe. The rubber disc is then pierced with the needle of the syringe and the sample injected into the tube. The same procedure must be performed with the solvent which is injected at intervals of about 2 minutes in 10 consecutive portions. When the injections have been completed the cooling tube is detached and flushed out with a small volume of solvent.

On the average each sample requires 1 to 2 hours work (preparation, control of apparatus, cleaning components of apparatus) by one person.

The invention aims at eliminating these defects and at reducing the expenditure in time and labor involved in the purifying of samples by the flushing and codistillation process, in other words at substantially raising the number of samples that can be purified within a given period of time whilst achieving an acceptable degree of purity for a quantitative determination.

According to the invention these objects are attained by the provision for the reception of the samples of detachable coils through which an inert gas stream carrying a solvent supplied substantially continuously from a supply vessel is conducted, and of purifying tubes which are connected to said sample coils and extend through a stove and terminate in cooling coils located inside a condenser.

The following advantages are achieved by using the apparatus according to the invention:

1. Continuous washing with the solvent ensures that the residence time of any temperature-sensitive substances which are to be determined is reduced to the minimum compatible with determination.
2. Reproducibility of the results is improved by the complete automation of the procedural steps and the elimination of human error in manual control.
3. The apparatus can operate day and night without supervision, thereby reducing the labor cost and general overheads by saving time.
4. The proposed change in procedure is responsible for the possibility of securing the advantages of automation.

BRIEF DESCRIPTION OF THE DRAWING

In order that the invention may be more readily understood an embodiment of the apparatus according to the invention will be hereunder described in greater detail with reference to the accompanying drawing, in which.

DESCRIPTION OF THE PREFERRED EMBODIMENT

Figure 1:
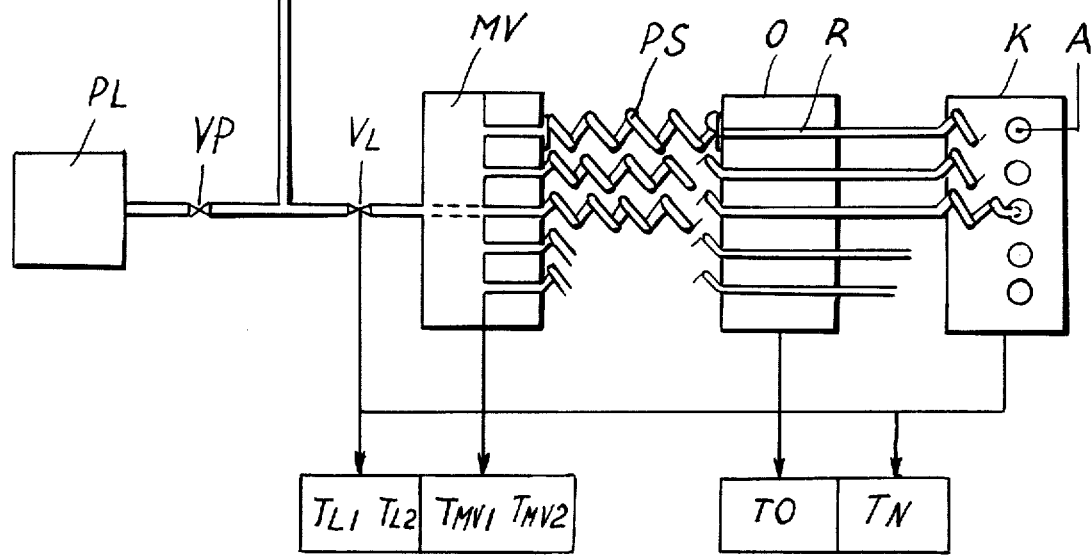
FIG. 1 is a schematic representation of an embodiment of apparatus according to the invention.

The apparatus illustrated in FIG. 1 is functionally based on the principle of combined flushing and codistillation. The liquid raw extract in FIG. 1 is first conveyed in a continuous inert gas stream into a hot zone, where the constituents dissolved in the extract are precipitated on a large surface. A volatile solvent which is then conducted over the surface picks up the desired more volatile trace components from the precipitate in a combination flushing and codistillation process and carries them into a low temperature condenser. A fresh precipitation surface must be provided for each sample.

The inert gas stream, e.g. nitrogen, obtained from a source of supply G (FIG. 1) is introduced in a known manner for instance into a pressurized gas container fitted with a pressure reducing valve and a gas distributing system. The gas stream is controlled by a fine regulating valve $V_G$ and a flow meter F. The purpose of the gas is to convey the several extract samples contained in the PTFE coils PS to the point of precipitation 0 and also to carry the solvents obtained from a reservoir PL. The velocity of transportation is controlled by the regulating valve $V_G$ in conjunction with F. In association with a valve VP the reservoir PL forms a solvent metering device. The addition of solvent is started or stopped by a pneumatically operating magnetic valve $V_L$ supplied from PL. The opening and closing times of this valve at intervals of 0 to 30 hours can be controlled by preset time switches $T_{L1}$ and $T_{L2}$.

The inert gas stream is then admitted by a multiple way valve MV in predetermined order to each of the continuously connected sample coils PS. A servo motor causes the central supply pipe to be alternately connected to each of the valve exits, assumed in the drawing to number 20. Two time switches $T_{MV1}$ and $T_{MV2}$ control the time for which the servo motor holds the connection to each exit as well as the duration of the change-over to the next exit. These switching times therefore determine the interference-free residence times of the samples at the place of precipitation 0.

The samples (up to 20 in the drawing) are introduced into the several sample coils by calibrated syringes before the apparatus is started up. These coils are flexible PTFE tubes which each have a capacity of 2.5 ml. On the one hand they are connected in a gas-tight manner by special threaded pipe unions to the exits of MV and on the other hand by commercial patented couplings of PTFE to (likewise 20) purifying unbranched glass tubes R. Up to about two thirds of the length of each of these tubes is filled with materials having a large surface area such as moderately tightly packed quartz wool or commercially available superficially etched glass balls, the empty parts of the tubes being equally divided between the two tube ends. The large surface area materials assure that the extract substances dissolved from the sample are deposited in the purifying tubes.

The tubes are fitted into holes in the solid aluminum block of the flushing and codistillating stove 0. The temperature is maintained by a controller TO in the range between about 20° and 300°C.

Similar patented couplings to those at the tube entries couple the tube ends to flexible PTFE tubes. For the purpose of quantitatively condensing the codistillation vapors they form coils cooled in an electronically controlled cold bath K of an alcoholic medium at −30°C. Receiving tubes A into which the PTFE tubes discharge are similarly cooled.

When the sample from the sample coil has been transferred into the hot pipe the substantially continuously controlled solvent supply continues until the empirically determined quantitative separation of the desired traces from the conjoint extractives from the raw extract has taken place. At the end of the purifying operations in the case of all (20) samples all electrically operated or controlled devices are stopped by a preadjustable time switch $T_N$. $T_N$ together with the parts $T_{MV1}$, $T_{MV2}$, $T_{L1}$, $T_{L2}$, $V_L$ and F are combined in one central control unit.

The purifying step on a sample proceeds automatically as follows:
1. Switch on power from the mains.
2. Turn on gas supply and adjust rate of flow.
3. Regulate flow rate of solvent to the desired rate.
4. Set time switch for solvent circulation to the desired value; these are the residence time and the time interval for connecting up the next sample coil.
5. Switch on stove and raise to necessary temperature level.
6. Switch on cold bath and adjust.
7. Connect sample coils to the purifying tubes in the oven and flush with solvent. After detaching the sample coils from the multiple way valve feed samples into coils and reconnect. Change the receiving tubes.
8. Calculate the total working time and set stop relay $T_N$ accordingly. If the test conditions are not changed the functions 1 to 6 can be centrally switched on and off by $T_N$.
9. Start up the automatic purifying operations.
10. At the end of these operations reduce the purified samples in the condensers to a given volume and inject an aliquot part into a suitable gas chromatographic identifying and analysing apparatus.

Figure 2:
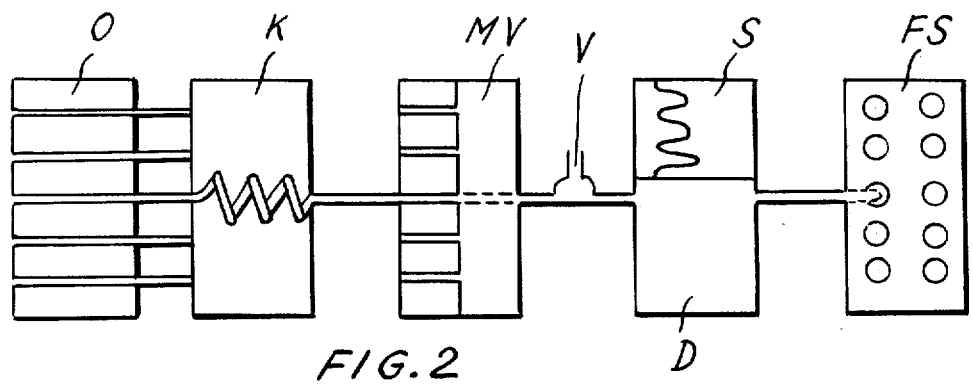
FIG. 2 is a diagram illustrating the disposition of an on-line detection system.

The continuous current of solvent also permits the desired substances to be determined directly after the purification of the sample in an on-line detection system, as illustrated in FIG. 2.

The vapors emerging from the purifying tube are condensed in a PTFE coil in the cooling bath K. The condensate is conveyed through a multi-port valve MV which connects the used purifying tube R to the T-piece V for the removal of air bubbles by vacuum means. From here the liquid stream enters the detector D (ultraviolet or differential refractometer), where the presence of the desired substances is established. The detector D is associated with an indicating instrument S (recording instrument). After having passed through the detector the several samples can be collected in a fraction collector FS if desired.

As a result of these steps it has been found that the times for purifying the samples for instance for the examination of different varieties of fruit or vegetable residues can be curtailed to about 1/6th of the times previously needed. Moreover, the results obtained are more accurate because the reproducibility of the results is better.

The invention may be embodied in other specific forms without departing from the spirit or essential characteristics thereof. The embodiment is therefore to be considered in all respects as illustrative and not restrictive.

What is claimed is:

1. Apparatus for automatically purifying extracts of vegetable and animal specimens for the determination, free from interference by substances including waxes, fats and dyes which interfere with the determination of the active substances, of traces of selected extract constituents by a combined flushing and codistilling process of the extracts with solvents, comprising:
   a. a plurality of sample coil tubes for the reception of samples, each sample coil tube having inlet and outlet ends,
   b. means for feeding a mixture of solvent and inert gas to said sample coil tubes,
   c. multiple way valve means detachably connected to the inlet ends of said sample coil tubes for connecting said mixture feeding means to each of said sample coil tubes in sequence,
   d. a plurality of purifying tubes for receiving precipitated constitutents from said samples, each purifying tube having inlet and outlet ends, the inlet end of each purifying tube being detachably connected to the outlet end of one of said sample coil tubes,
   e. means surrounding said purifying tubes for heating said purifying tubes to flush and codistil vapors,
   f. a plurality of cooling tubes for quantitatively condensing vapors from said purifying tubes forming a condensate therein, each cooling tube having inlet and outlet ends, the inlet end of each cooling tube being connected to the outlet end of one of said purifying tubes, g. means surrounding said cooling tubes for cooling said cooling tubes, h. a plurality of receiving tubes, each connected to the outlet end of one of said cooling tubes, for receiving the condensate discharged from said cooling tubes i. timing means for controlling said multiple way valve means to control the time interval during which said mixture feeding means is connected to each sample coil tube and the time interval between connections of said mixture feeding means to successive sample coil tubes, and j. control means for regulating the temperature of said heating means and said cooling means.

2. Apparatus according to claim 1 wherein the purifying tubes are unbranched glass tube sections which are at least partly filled with materials having a large surface area for depositing the extract substances dissolved from the sample in the purifying tube.

3. Apparatus according to claim 2 wherein the purifying tubes are unbranched glass tube sections which are at least partly filled with quartz wool.

4. Apparatus according to claim 2 wherein the purifying tubes are unbranched glass tube sections which are least partly filled with etched glass balls.

5. Apparatus according to claim 2 wherein said means for feeding a mixture of solvent and inert gas comprises a first conduit for feeding said solvent, a second conduit for feeding said inert gas, said first and second conduits merging into a further conduit connected to said multiple way valve, and valve means in each of said first, second and further conduits for regulating flow of said solvent, inert gas and mixture respectively.

6. Apparatus according to claim 5 further comprising timing means controlling said valve means in said further conduit for regulating the flow of said mixture to said multiple way valve.

7. Apparatus according to claim 6 further comprising means for detecting the presence of at least one substance contained in the condensate discharged from said cooling tubes and T-shaped conduit means extending from said cooling tubes to said detector means whereby a vacuum may be applied to remove air bubbles from said condensate.

* * * * *